(12) United States Patent
Mizuo et al.

(10) Patent No.: US 6,528,334 B1
(45) Date of Patent: Mar. 4, 2003

(54) SEMICONDUCTOR INSPECTION SYSTEM, AND METHOD OF MANUFACTURING A SEMICONDUCTOR DEVICE

(75) Inventors: Mariko Mizuo, Hyogo (JP); Yoko Miyazaki, Tokyo (JP)

(73) Assignees: Mitsubishi Denki Kabushiki Kaisha, Tokyo (JP); Ryoden Semiconductor System Engineering Corporation, Hyogo (JP)

( * ) Notice: Subject to any disclaimer, the term of this patent is extended or adjusted under 35 U.S.C. 154(b) by 180 days.

(21) Appl. No.: 09/677,846

(22) Filed: Oct. 3, 2000

(30) Foreign Application Priority Data

Mar. 29, 2000 (JP) .......................... 2000-090920

(51) Int. Cl.$^7$ .......................... H01L 21/66; G01N 21/00
(52) U.S. Cl. .......................... 438/16; 356/239.8
(58) Field of Search .......................... 356/239.8, 239.7, 356/237.1, 239.1; 438/14, 16

(56) References Cited

U.S. PATENT DOCUMENTS 6,169,601 B1 * 1/2001 Eremin et al. ........... 356/237.1

FOREIGN PATENT DOCUMENTS

| JP | 4-324653 | 11/1992 |
|---|---|---|
| JP | 6-252230 | 9/1994 |
| JP | 10-325712 | 12/1998 |
| JP | 11-248038 | 10/1999 |

* cited by examiner

Primary Examiner—Kamand Cuneo
Assistant Examiner—Evan Pert
(74) Attorney, Agent, or Firm—McDermott, Will & Emery (57) ABSTRACT

There are described a semiconductor inspection system for inspecting recessed defects formed in a semiconductor wafer and a semiconductor device manufacturing method including an inspection step of inspecting recessed defects formed in a semiconductor wafer. The semiconductor inspection system and the semiconductor device manufacturing method enable the following operations: an operation of radiating a laser beam onto a semiconductor wafer; an operation of detecting light scattered from foreign particles, as a result of a laser beam being radiated onto the semiconductor wafer; an operation of converting the detected scattered light into an electric signal; and an operation of outputting information about the recessed defects formed in the semiconductor wafer by means of subtracting the data pertaining to only the foreign particles located on the semiconductor wafer from the data pertaining to both the foreign particles and recessed defects formed in the semiconductor wafer.

9 Claims, 10 Drawing Sheets measurement by dust particle sensitivity curve:Result A data of dust particles only measurement by defect sensitivity curve:Result B data of both dust particles
and recessed defects

Result B—Result A=Result C data of recessed
defects only

FIG. 1A configuration of semiconductor inspection system

FIG. 1B detailed configuration of inspection section

FIG. 2
procedure of inspection

FIG. 2A
reference wafer for inspecting dust particle

FIG. 2B
reference wafer for inspecting recessed defect

FIG. 2C
dust particle sensitivity curve

FIG. 2D
recess sensitivity curve

FIG. 3A measurement by dust particle sensitivity curve:Result A data of dust particles only

FIG. 3B measurement by defect sensitivity curve:Result B data of both dust particles
and recessed defects

FIG. 3C

Result B−Result A=Result C data of recessed
defects only

FIG. 7A configuration of semiconductor inspection system

FIG. 7B detailed configuration of inspection section

FIG. 8A scattering of obliquely
radiated beam by dust particle

FIG. 8B scattering of obliquely
radiated beam by recessed defect

FIG. 9A measurement by obliquely radiated beam:Result A data of dust particles only

FIG. 9B measurement by normally radiated beam:Result B data of both dust particles and defects

FIG. 9C

Result B−Result A=Result C data of recessed defects only

FIG. 10A
Background Art configuration of semiconductor inspection system

FIG. 10B
Background Art detailed configuration of inspection section

FIG. 11
Background Art procedure of inspection

FIG. 11A
Background Art reference wafer for inspecting dust particle

FIG. 11B
Background Art relationship between intensity of scattered light and resultant count value

FIG. 11C
Background Art sensitivity curve

SEMICONDUCTOR INSPECTION SYSTEM, AND METHOD OF MANUFACTURING A SEMICONDUCTOR DEVICE

BACKGROUND OF THE INVENTION

1. Field of the Invention

The present invention relates to a semiconductor inspection system for inspecting defects, such as recesses in a semiconductor wafer, as well as to a method of manufacturing a semiconductor device including a step of inspecting recesses in a semiconductor wafer.

2. Background Art

If foreign particles or defects arise in a semiconductor wafer, the foreign particles or defects causes an impediment in a process of manufacturing a semiconductor device from a semiconductor wafer. Further, such foreign particles or defects exert significant influence on the characteristic of the semiconductor device manufactured from the semiconductor wafer. An inspection step of measuring the size and density of foreign particles present on a semiconductor wafer is indispensable for the process of manufacturing a semiconductor device.

Figure 10A:
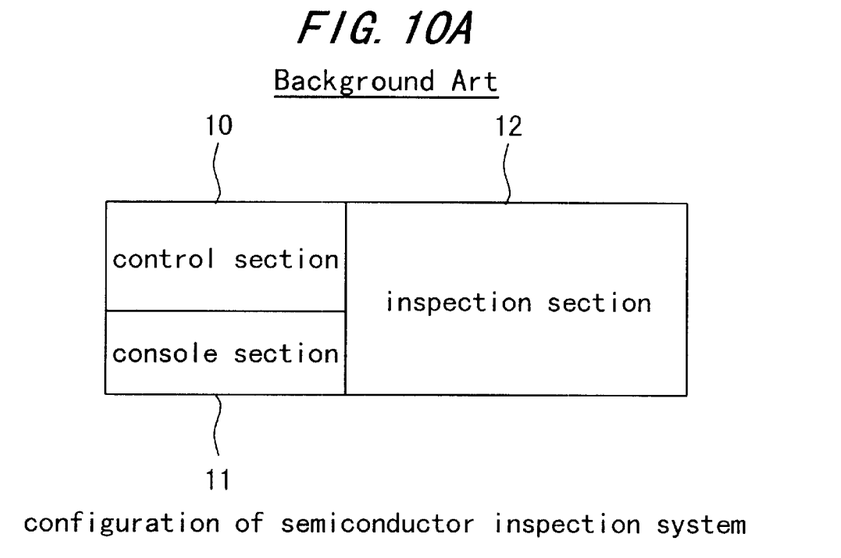
FIG. 10A and FIG. 10B show a configuration of a conventional semiconductor inspection system.

FIG. 10A is a block diagram showing a configuration of a conventional semiconductor inspection system.

Figure 10B:
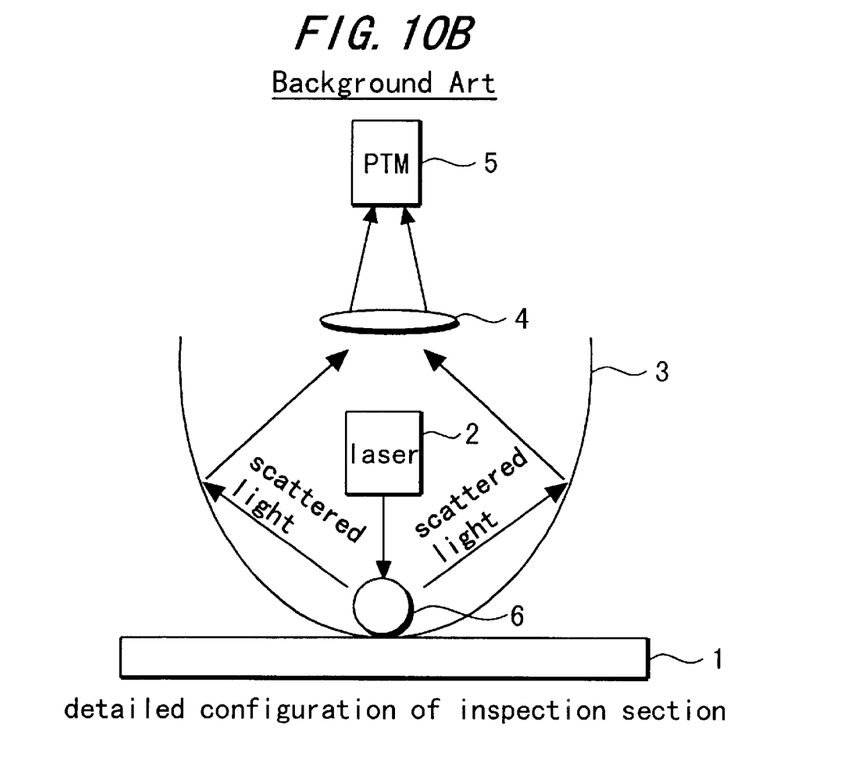

The conventional semiconductor inspection system shown in FIG. 10A comprises a control section 10 for storing data and controlling the overall inspection system; a console section 11 for mechanically actuating a wafer transporting device; and an inspection section 12 for inspecting foreign particles on a semiconductor wafer. FIG. 10B simultaneously shows a detailed configuration of the inspection section 12. In the drawing, reference numeral 1 designates a semiconductor wafer which is an object of inspection, and reference numeral 6 designates a foreign particle adhering to the surface of the semiconductor wafer 1. Reference numeral 2 designates a laser beam radiation section for radiating a laser beam onto the semiconductor wafer 1. The laser beam radiation section 2 can radiate a laser beam on the semiconductor wafer while scanning the semiconductor wafer. Reference numeral 3 designates a reflection section for reflecting the light scattered from the foreign particle 6; 4 designates a light converging section for converging the light reflected from the reflection section 3; and 5 designates a detection section (photo-multiplier: PTM) for detecting the thus-converged light.

Figure 11:
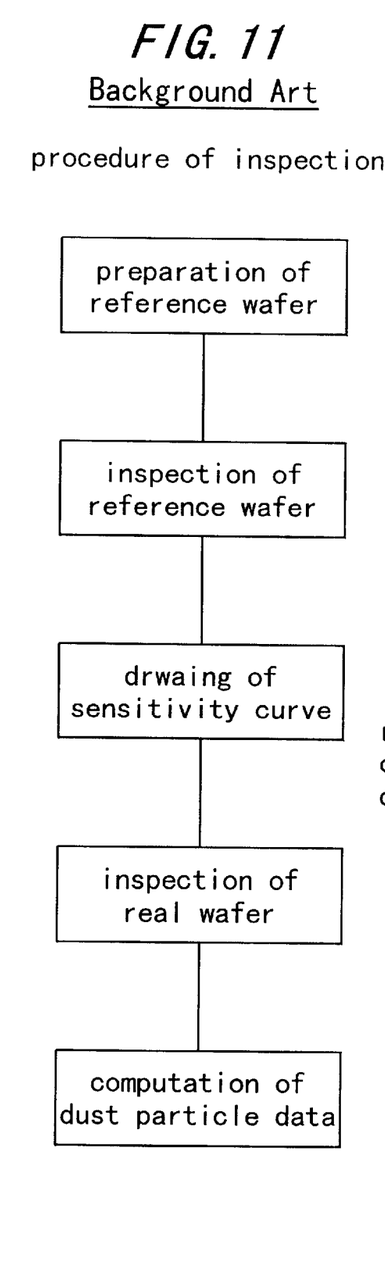
FIGS. 11, 11A, 11B, and 11C show procedure and principle for , inspecting an extraneous object on a semiconductor wafer.

On the basis of a flowchart shown in FIG. 11, procedures for inspecting an extraneous object on a semiconductor wafer through use of the conventional semiconductor inspection system will now be described.

Figure 11A:
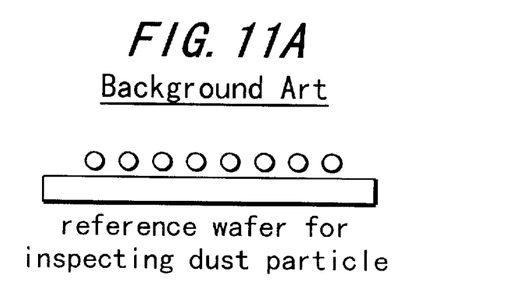

First, a reference wafer to be used for inspecting an foreign particle as shown in FIG. 11A is prepared. The reference wafer is prepared by means of coating a wafer, which is identical in size with a semiconductor wafer to be inspected, with a plurality of foreign particles of identical size; that is, polystyrene particles (PSL). A plurality of wafers are prepared, each wafer being coated with foreign particles of a different size.

Figure 11B:
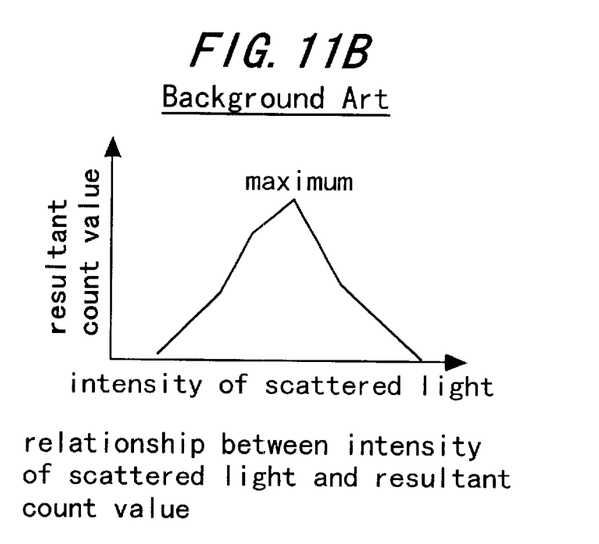

The sizes of different foreign particles provided on the reference wafers are measured, through use of the semiconductor inspection system shown in FIG. 10. The reference wafer is inspected by means of a laser beam being radiated, in a scanning manner, on the semiconductor wafer 1 from the laser beam radiation section 2. The detection (PTM) section 5 detects the intensity of the light scattered from the semiconductor wafer 1. At this time, the relationship between intensity of scattered light and the resultant count value is plotted for each reference wafer, as shown in FIG. 11B.

On the basis of the graph relating to the relationship between intensity of scattered light and the resultant count value, the graph being defined for each of the reference wafers coated with a foreign particle of a different size, the intensity of scattered light corresponding to the maximum count value is defined as the intensity of scattered light for a foreign particle of each size.

Figure 11C:
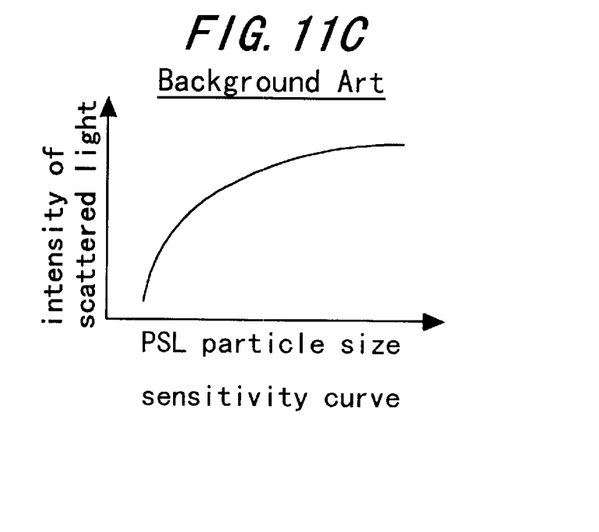

Next, a sensitivity calibration curve is prepared. As shown in FIG. 11C, the sensitivity calibration curve is prepared by means of plotting the relationship between PSL particle size and intensity of scattered light.

A real wafer which is to be actually subjected to foreign particle inspection is measured, whereby the relationship between the intensity of scattered light and the resultant count value is examined. By reference to the sensitivity calibration curve, there is performed computation of foreign particle data; that is, estimation of distribution (i.e., the sizes and locations) of foreign particles on the real wafer.

The conventional semiconductor inspection system and the conventional foreign particle inspection method have been embodied as mentioned previously.

The conventional system and method enable measurement of foreign particles which are present on a wafer surface in the form of projections. In a case where crystal-originated particles (COPs), which are crystal imperfections of a wafer, or recesses, such as micro-scratches formed during a chemical-mechanical polishing step during wafer processing, are present on a wafer, the conventional system and method encounter the following problems.

The light scattered from recessed defects or damage of a wafer is weaker than the light scattered from projecting foreign particles which are present on a wafer surface. In a case where foreign particles and recessed defects are mixedly present on a wafer, even when an attempt is made to measure only recessed defects, both foreign particles and recessed defects are measured. Thus, sharp, distinctive indication of only recessed defects is infeasible.

The present invention has been conceived to solve the drawback of the background art as described above and is aimed at providing a semiconductor inspection system which can sharply distinguish recesses from foreign particles on a wafer and measure the distribution of recessed defects, such as crystal imperfections or damages, over a wafer while the size and position of desired defects are specified. Further, the present invention is aimed at providing a semiconductor device manufacturing method including an inspection step of inspecting defects of a semiconductor wafer through use of the foregoing semiconductor inspection system.

SUMMARY OF THE INVENTION

According to one aspect of the present invention, a semiconductor device inspection system comprises a laser beam radiation section, a detection section and a control section. The laser beam radiation section radiates a laser beam onto a semiconductor wafer to be measured. The detection section detects light scattered from foreign particles or recessed defects formed in the semiconductor wafer, as a result of a laser beam being radiated onto the semiconductor wafer, and converts the detected scattered light into an electric signal. Further, the control section processes the electric signal in the form of data, and outputs information about the recessed defects formed in the semiconductor wafer, by means of subtracting the data pertaining to only the foreign particles located on the semiconductor wafer from the data pertaining to both the foreign particles and recessed defects formed in the semiconductor wafer.

According to another aspect of the present invention, a semiconductor device inspection system comprises a laser beam radiation section, a detection section and a control section. The laser beam radiation section radiates a laser beam onto a semiconductor wafer to be measured. The laser beam radiation section can radiate a laser beam onto the primary surface of the semiconductor wafer by selection of either a normal direction or an oblique direction. The detection section detects light scattered from foreign particles or recessed defects formed in the semiconductor wafer as a result of a laser beam being radiated onto the semiconductor wafer and converts the detected scattered light into an electric signal. The control section processes the electric signal in the form of data, and outputs information about the recessed defects formed in the semiconductor wafer, by means of subtracting the data pertaining to only the foreign particles located on the semiconductor wafer from the data pertaining to both the foreign particles and recessed defects formed in the semiconductor wafer.

According to still another aspect of the present invention, in a method of manufacturing a semiconductor device, a laser beam is radiated onto a semiconductor wafer to be measured. Light scattered from foreign particles or recessed defects formed in the semiconductor wafer is detected, and the detected scattered light is converted into an electric signal. The electric signal is processed in the form of data, and outputted is information about the recessed defects formed in the semiconductor wafer by means of subtracting the data pertaining to only the foreign particles located on the semiconductor wafer from the data pertaining to both the foreign particles and recessed defects formed in the semiconductor wafer.

According to further aspect of the present invention, in a method of manufacturing a semiconductor device, a laser beam is radiated onto a semiconductor wafer to be measured in a normal direction, and light scattered from foreign particles or recessed defects formed in the semiconductor wafer is detected. The detected scattered light is converted into an electric signal, to thereby prepare data pertaining to both foreign particles and recessed defects formed in the semiconductor wafer. Further, a laser beam is radiated onto the primary surface of the semiconductor wafer in an oblique direction, and the light scattered from foreign particles located on the semiconductor wafer is detected. The detected scattered light is converted into an electric signal, to thereby prepare data pertaining to solely foreign particles located on the semiconductor wafer. Then, outputted is information about the recessed defects formed in the semiconductor wafer by means of subtracting the data pertaining to only the foreign particles located on the semiconductor wafer from the data pertaining to both the foreign particles and recessed defects formed in the semiconductor wafer.

Other and further objects, features and advantages of the invention will appear more fully from the following description.

DETAILED DESCRIPTION OF THE PREFERRED EMBODIMENTS

Preferred embodiments of the present invention will now be described in detail with reference to the accompanying drawings. In the drawings, the same or corresponding portion are designated by same reference numerals, and detailed explanation may be omitted or simplified.

First Embodiment

Figure 1A:
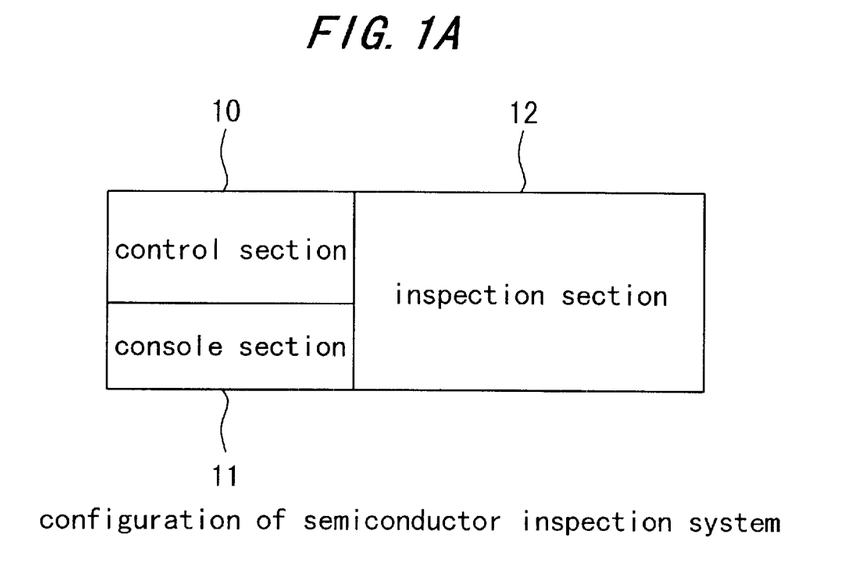
FIG. 1A and FIG. 1B show a configuration of a semiconductor inspection system according to a first embodiment of the present invention.

FIG. 1A is a block diagram showing a configuration of a semiconductor inspection system according to a first embodiment of the present invention.

The semiconductor inspection system shown in FIG. 1A comprises a control section 10, a console section 11, and an inspection section 12. Here, the control section 10 has storage means made up of semiconductor memory or a like device and control means (not shown) made up of a CPU or a like device. The control section 10 controls storage of data and the operation of the overall semiconductor inspection system.

The console section 11 performs mechanical actuation of a device, such as transportation of a semiconductor wafer. The inspection section 12 has a function of inspecting recessed defects in a semiconductor wafer.

Figure 1B:
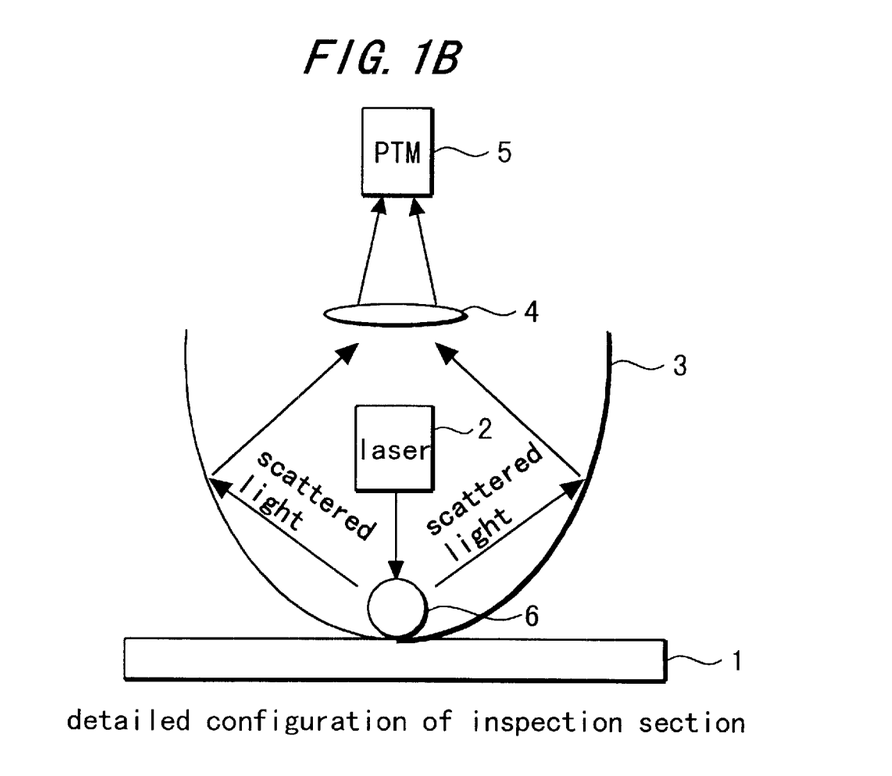

FIG. 1B shows the detailed structure of the inspection section 12 of the semiconductor inspection system described in connection with FIG. 1A. Here, reference numeral 1 designates a semiconductor wafer which is an object of inspection.

Reference numeral 2 designates a laser radiation section for radiating a laser beam onto the semiconductor wafer 1. The laser radiation section 2 can radiate a laser beam onto the semiconductor wafer 1 while scanning the same. Reference numeral 3 designates a reflection section for reflecting the light scattered from foreign particles on or recesses in the semiconductor wafer 1; and 4 designates a light converging section for converging the light reflected from the reflection section 3. An optical lens is used for the light converging section 4. Reference numeral 5 designates a detection section for converting the thus-converged light into an electric signal. A photo-multiplier (PTM) is used for the detection section 5.

Figure 2:
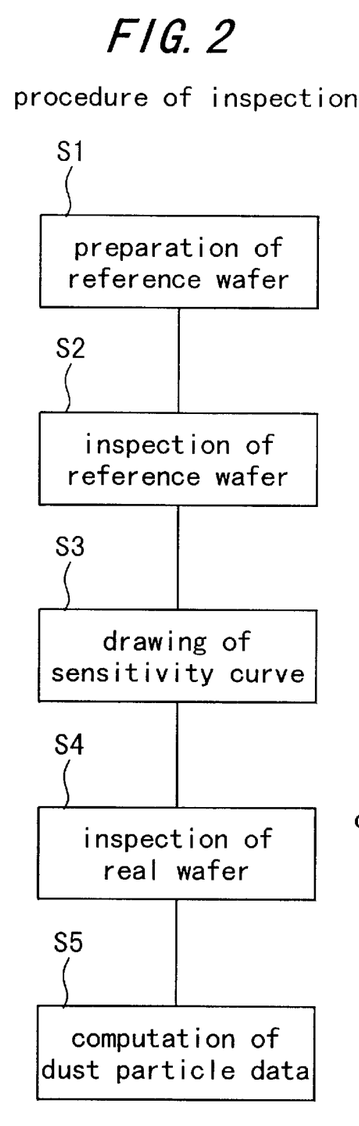
FIG. 2 and FIG. 2A through FIG. 2D show procedure and principle for inspecting recessed defects on a semiconductor wafer according to the first embodiment of the present invention.

FIG. 2 is a flowchart showing, in sequential order, steps of detecting the distribution and sizes of recessed defects in a semiconductor wafer, through use of the semiconductor inspection system according to the present invention.

Figure 2A:
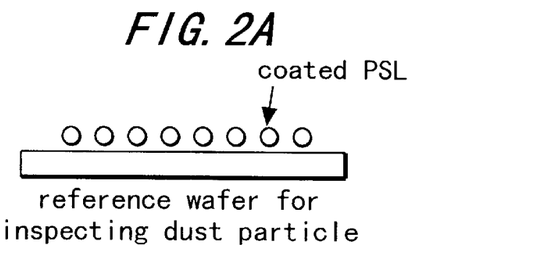
Figure 2B:
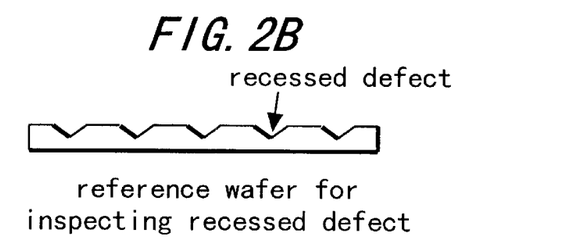

Explanation will now be given of a step S1 of preparing a reference wafer, by reference to the flowchart showing recessed defect inspection procedures shown in FIG. 2. A reference wafer (FIG. 2A) to be used for measuring foreign particles on a semiconductor wafer and a reference wafer (FIG. 2B) to be used for measuring recessed defects are prepared.

The reference wafer (FIG. 2A) to be used for measuring foreign particles is prepared by means of coating a wafer, which is identical in size with a semiconductor wafer to be measured, with a plurality of foreign particles of identical size; e.g., polystyrene (PSL) particles. A plurality of reference wafers are prepared (FIG. 2A), each wafer coated with foreign particles of a different size.

Similarly, the reference wafer (FIG. 2B) to be used for measuring recessed defects is prepared by means of forming a plurality of recesses of specific size and shape, at a specific pitch or at random pitches, on a wafer identical in size with a semiconductor wafer to be measured. These reference wafers are formed from a substrate having a film formed thereon, by use of a focused ion beam (FIB) or electron beam (EB) or by combination of a photolithography step and an etching step.

Figure 4A:
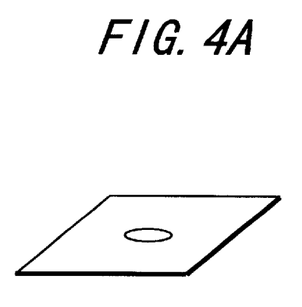
FIGS. 4A through 4C show example contours of recesses formed in the surface of a reference wafer.
Figure 4B:
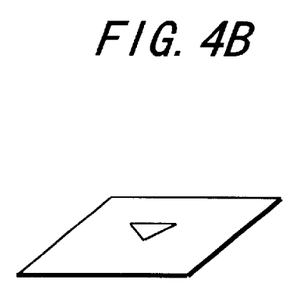
Figure 4C:
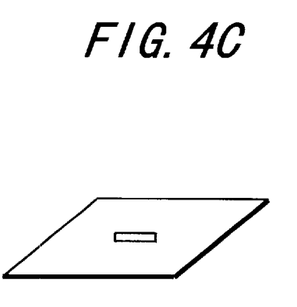

FIGS. 4A through 4C are perspective views showing example contours of recesses formed in the surface of a reference wafer. FIG. 4A shows a recess having a circular contour; 4B shows a recess having a triangular contour; and 4C shows a recess having a rectangular contour.

Figure 5A:
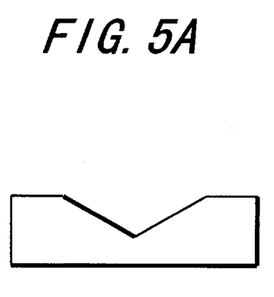
FIGS. 5A through 5C show cross-sectional views of wafers showing example cross sections of recesses formed in a reference wafer.
Figure 5B:
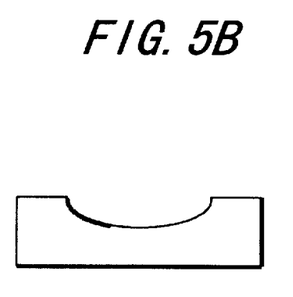
Figure 5C:
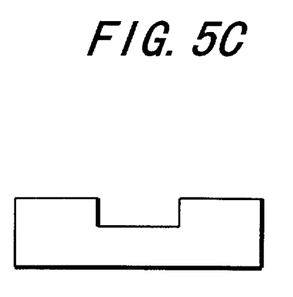

FIGS. 5A through 5C are cross-sectional views of wafers showing example cross sections of recesses formed in a reference wafer. FIG. 5A shows a recess having a wedge-shaped cross section; FIG. 5B shows a recess having a circular cross section; and FIG. 5C shows a recess having a rectangular cross section.

Figure 6A:
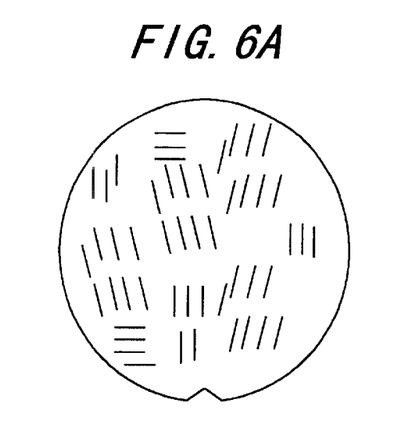
FIGS. 6A through 6C show plan views of orientations of recesses formed in the surface of the reference wafer.
Figure 6B:
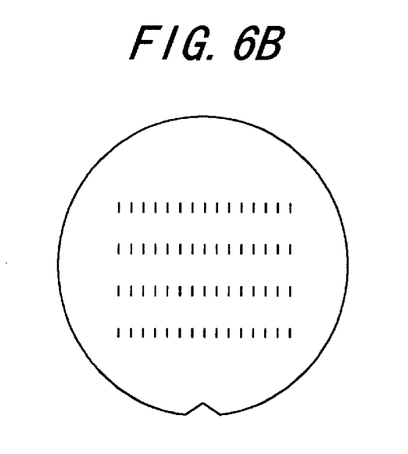
Figure 6C:
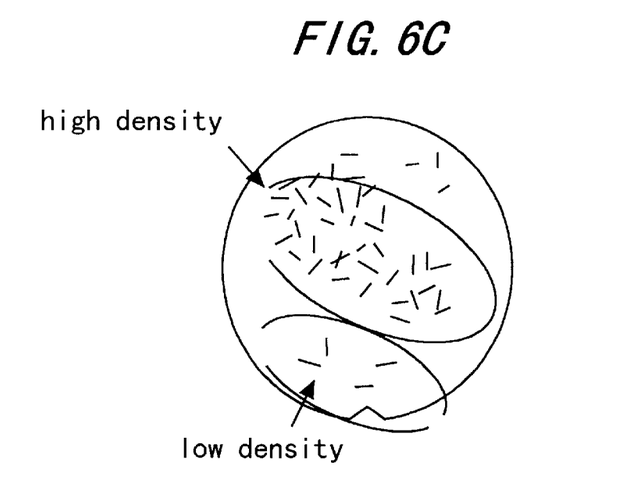

FIGS. 6A through 6C are plan views showing orientations of recesses formed in the surface of the reference wafer. FIG. 6A shows an example in which linear recesses of equal length are formed in the form of local groups, the recesses of each of the groups being aligned in a single direction. The example recesses shown in FIG. 6A are characterized in that they are analogous to actual recesses induced by crystal imperfections of a semiconductor wafer. FIG. 6B shows example recesses which are arranged into regular rows and aligned in a single direction. The arrangement of such recesses is similar to the scratches generated in a actual manufacturing process and is formed easily. FIG. 6C shows an example in which recesses are arranged so as to differ in layout density within the wafer surface. By means of recesses being arranged in such a way, a real-world layout of recesses can be created, thereby facilitating detection of recesses formed in a real wafer. In an actual inspection step, an optimum reference wafer is selected from these reference wafers in accordance with the object of inspection, as required.

Turning again to FIG. 2, processing proceeds to a step S2 of measuring the reference wafers. In this step, the inspection section 12 of the semiconductor inspection system measures the reference wafers to be used for measuring foreign particles and the reference wafers to be used for measuring recessed defects, thereby acquiring, for each of the reference wafers, data pertaining to the relationship between the intensity of the light scattered from foreign particles and recessed defects and the resultant count values. The thus-acquired data are stored in the control section 10 of the semiconductor inspection system.

The method of preparing data pertaining to reference wafers to be used for measuring foreign particles is the same as that described in connection with the background art. For each of PSL particle sizes, the relationship between intensity of scattered light and the resultant count value is plotted.

A method of measuring reference wafer to be used for measuring reference wafers to be used for measuring recessed defects is in principle the same as that used for measuring reference wafers to be used for measuring foreign particles. For any of the types of reference wafers to be used for measuring recesses described previously, a plurality of reference wafers are prepared, each wafer having recesses of a different size formed therein. The laser beam radiation section 2 radiates a laser beam on each of the reference wafers while scanning the same, through use of the semiconductor inspection system. The intensity of the light scattered from the wafer is detected by the detection section 5. At that time, the relationship between intensity of scattered light and the resultant count value is plotted for each of the reference wafers. Subsequently, on the basis of the relationship between intensity of scattered light and the resultant count value, the relationship being plotted for each of the plurality of reference wafers having recesses of difference sizes (i.e., difference diameters), the intensity of scattered light corresponding to the maximum count value is defined as the intensity of scattered light for a recess of the corresponding size.

Figure 2C:
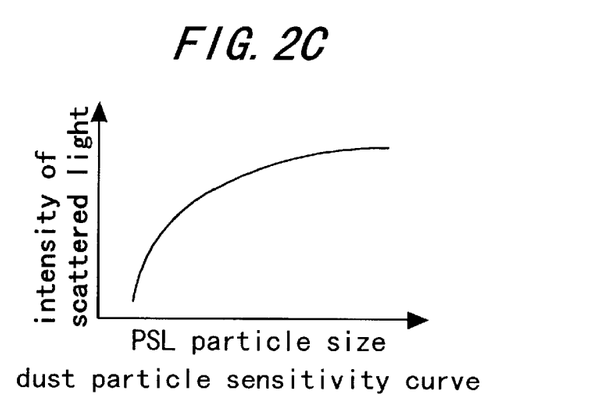
Figure 2D:
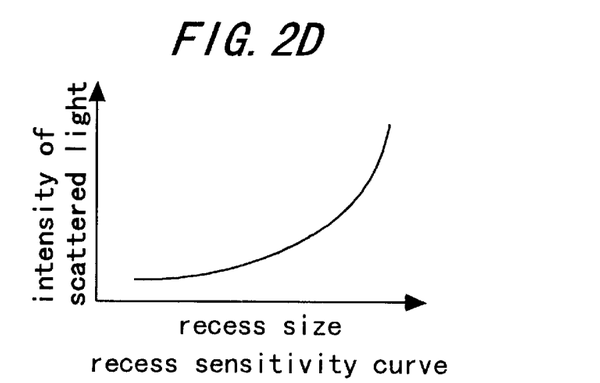

Subsequently, in the step S3 of preparing a sensitivity calibration curve as shown in FIG. 2, a foreign particle sensitivity calibration curve (FIG. 2C) and a recess sensitivity calibration curve (FIG. 2D) are prepared on the basis of the data stored in the step of measuring reference wafers. The foreign particle sensitivity calibration curve is prepared by means of plotting the relationship between sizes of foreign particles and intensity of scattered light. Further, the recess sensitivity calibration curve is prepared by means of plotting the relationship between the sizes (diameters) of recesses and the intensity of scattered light.

In the step S4 of measuring a real wafer shown in FIG. 2, a real wafer to be subjected to a recessed defect inspection operation is measured. Procedures for measuring a real wafer are substantially the same as those employed in the step of measuring reference wafers. Specifically, a laser beam is radiated in a scanning manner onto a real wafer to be measured. The intensity of light scattered from recesses located on the wafer is counted, and data pertaining to the count values are stored in the control section 10 of the semiconductor inspection system.

In the step S5 of calculating defects shown in FIG. 2, the data obtained in the step of measuring the real wafer are compared with the foreign particle sensitivity calibration curve (FIG. 2C) which has been prepared in the step of preparing a sensitivity calibration curve and which defines the relationship between sizes of foreign particles and intensity of light scattered from the foreign particles, as well as with the recess sensitivity calibration curve (FIG. 2D) defining the relationship between recesses and the intensity of light scattered from the recesses, to thereby compute the distribution of defects over the real wafer.

The technique of computing the distribution of defects over the real wafer will be described in detail by reference to FIGS. 3A through 3C.

Figure 3A:
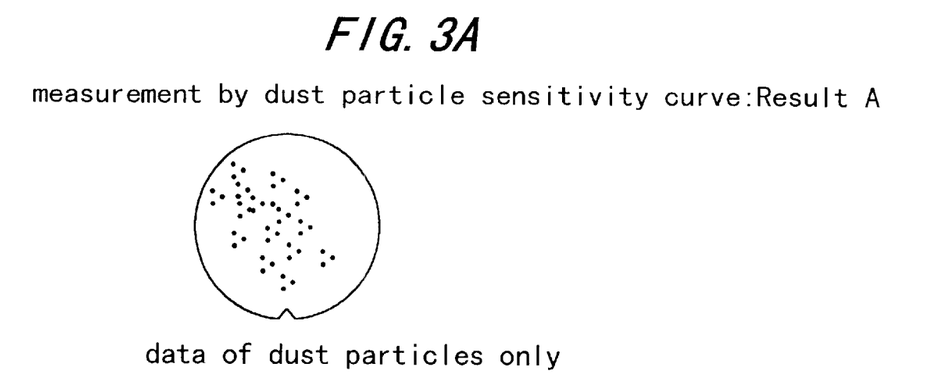
FIG. 3A through FIG. 3C show principle for computing the distribution of recessed defects over a real wafer.

FIG. 3A is an illustration in which the distribution of foreign particles within a wafer surface is plotted on the basis of the result of measurement of a real wafer and by reference to the foreign particle sensitivity calibration curve (this illustration is called Result A). Throughout FIGS. 3A through 3C, the distribution of foreign particles within a wafer surface is designated by solid circles, and only defects are represented by hollow circles.

Figure 3B:
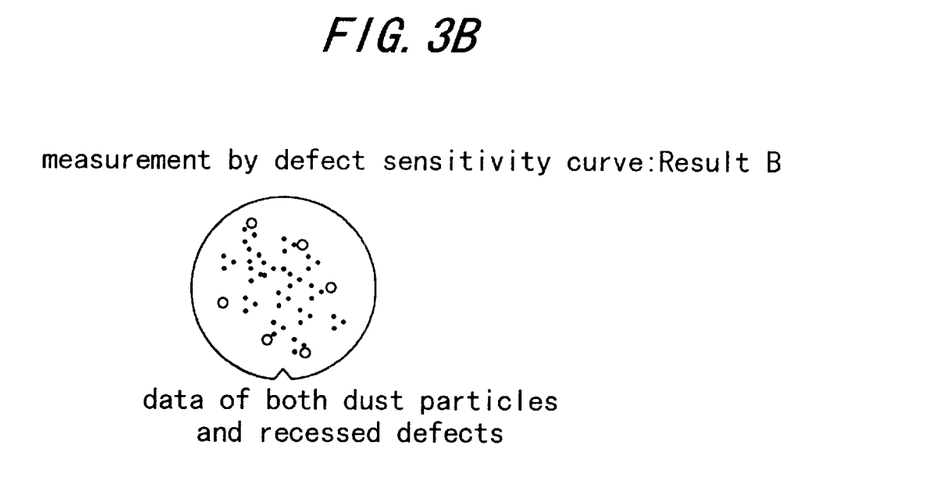

As shown in FIG. 3B, the distribution of recessed defects in a wafer surface is examined by reference to the recessed defect sensitivity calibration curve. The intensity of a laser beam scattered from a recessed defect is usually weaker than the intensity of a laser beam scattered from a foreign particle. Accordingly, in a case where foreign particles are detected through use of the foreign particle sensitivity calibration curve, even if recessed defects exist in a wafer surface, recessed defects located in a wafer surface are not detected, wherewith only the foreign particles are detected and the detection result is output. In contrast, in a case where an attempt is made to detect recessed defects through use of the recess sensitivity calibration curve, if foreign particles coexist with recessed defects on a wafer surface, foreign particles as well as recessed defects are plotted as shown in FIG. 3B, because the intensity of the light scattered from foreign particles is greater than the intensity of the light scattered from recessed defects (this plot is called Result B).

Figure 3C:
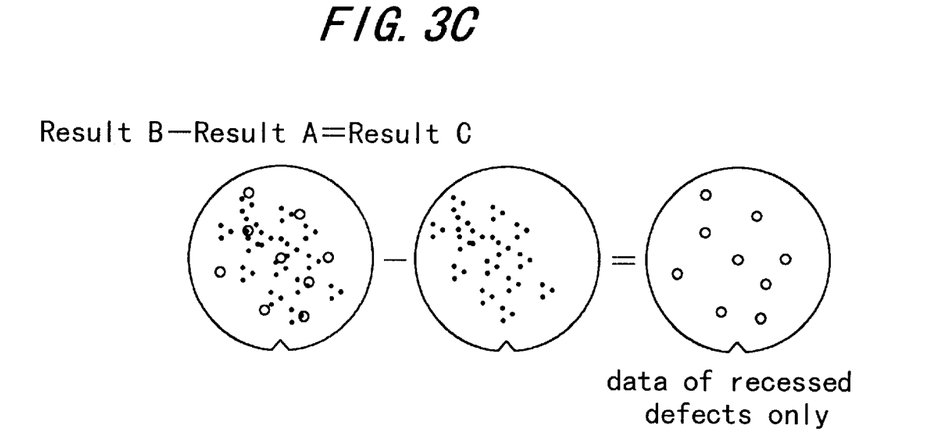

As shown in FIG. 3C, the data (Result A) pertaining to only foreign particles are subtracted from the data (Result B) pertaining to both recessed defects and foreign particles plotted in FIG. 3B. As a result (Result C), only data pertaining to recessed defects located in a wafer surface remain. The resultant data are stored and output to the outside of the semiconductor inspection system.

In this way, the distribution of recessed defects which are present in a wafer surface can be measured in the first embodiment. The computing operation, storage of computation results, and output of the same are controlled by the control section 10 of the semiconductor inspection system.

Second Embodiment

In the first embodiment, there is employed the technique of preparing data pertaining to solely recessed defects, by means of subtracting the data pertaining to only foreign particles, as measured through use of the foreign particle sensitivity calibration curve, from the data pertaining to foreign particles and recessed defects, as measured through use of recessed defect sensitivity calibration curve.

Figure 7A:
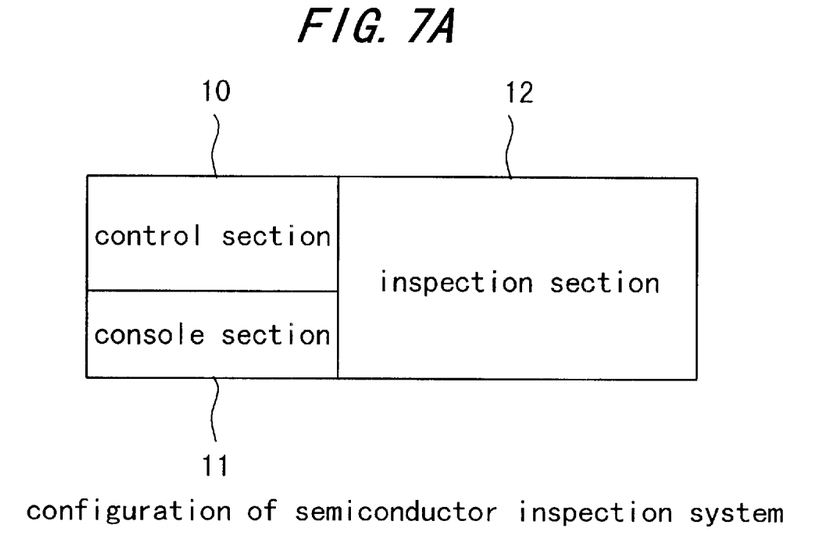
FIG. 7A and FIG. 7B show a configuration of a semiconductor inspection system according to a second embodiment of the present invention.
Figure 7B:
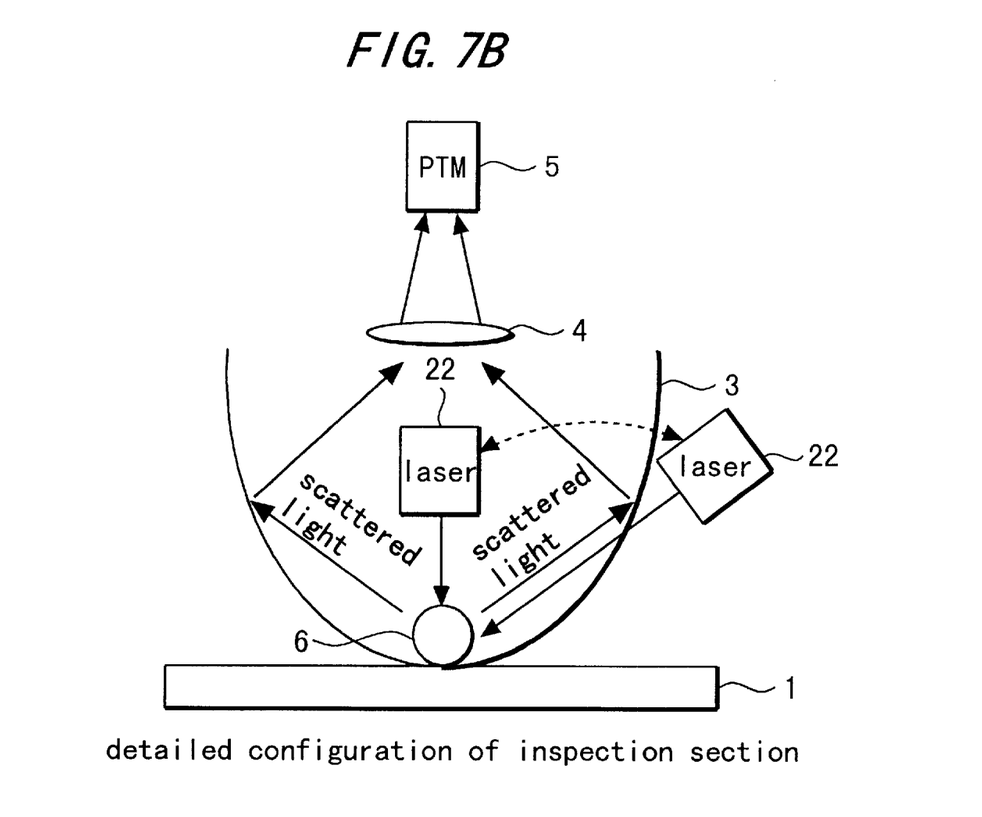

The present embodiment describes another method of sharply distinguishing foreign particles from recessed defects. FIGS. 7A and 7B show a semiconductor inspection system used in the present embodiment. As distinct from the semiconductor inspection system described in connection with the first embodiment, the semiconductor inspection system in the second embodiment is configured such that a laser beam radiation section 22 is movable so as to be able to radiate a laser beam onto a wafer in either of two directions; that is, a normal direction and an oblique direction relative to a wafer. Alternatively, the laser beam radiation section 22 may be configured through use of a plurality of independent radiation sections. In other respects, the semiconductor inspection system according to the second embodiment is identical in structure with that described in connection with the first embodiment, and hence repetition of its explanation is omitted.

Figure 8A:
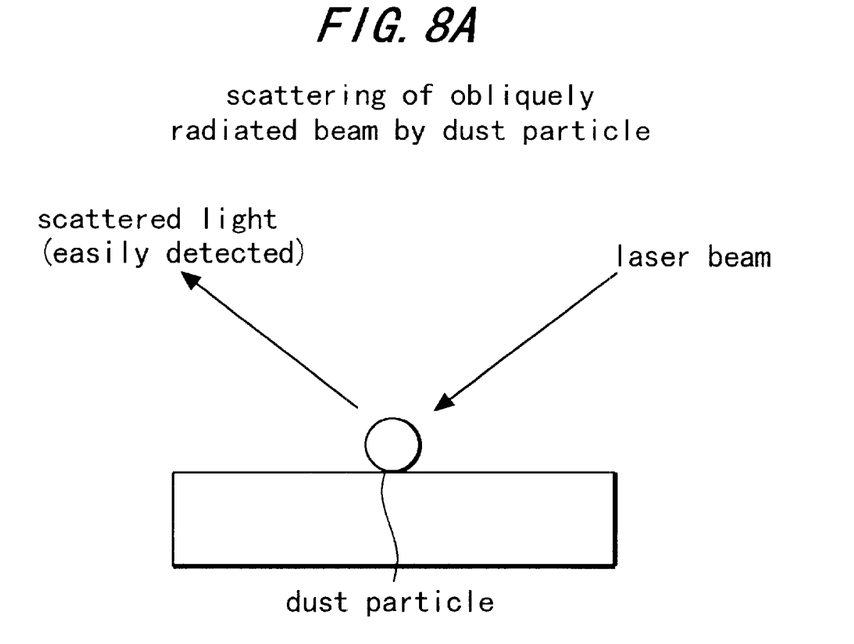
FIG. 8A and FIG. 8B show scattering of obliquely-radiated laser beam by foreign particles and recessed defects.
Figure 8B:
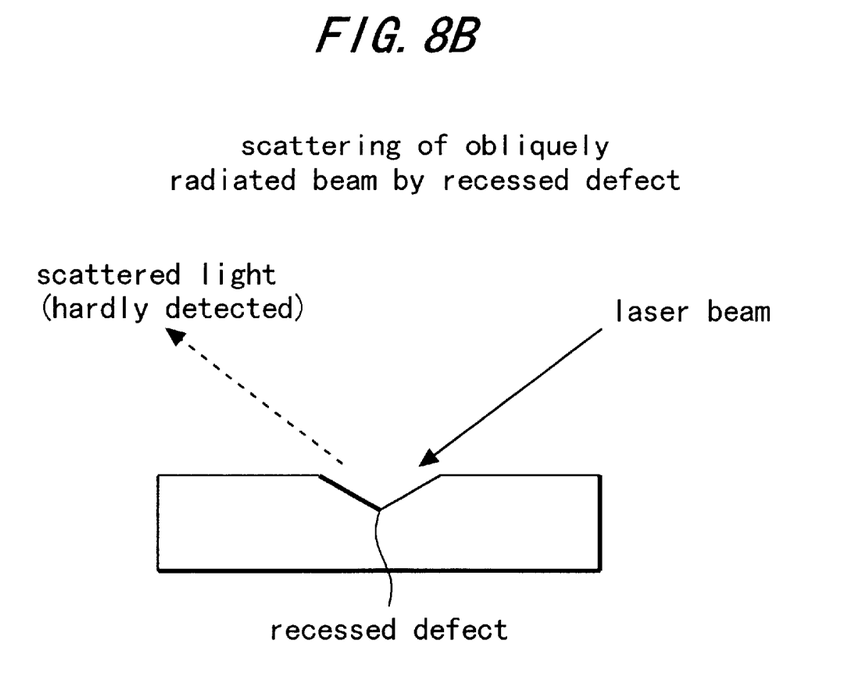

In the second embodiment, in a step S3 corresponding to the real wafer measurement step employed in the first embodiment (FIG. 2), a laser beam is radiated onto the primary surface of a semiconductor wafer to be measured, from a normal direction and in a scanning manner, to thereby acquire data pertaining to foreign particles and recessed defects which are present on the wafer. Similarly, there are obtained data pertaining to foreign particles located on the wafer. As shown in FIG. 8A, as in a case where foreign particles scatter the laser beam radiated from a normal direction, foreign particles scatter the laser beam that is radiated obliquely. However, as shown in FIG. 8B, the recessed defects encounter difficulty in scattering the obliquely-radiated laser beam, and hence detection of recessed defects is difficult. For this reason, the data obtained as a result of a laser beam being radiated onto the wafer from a normal direction contain data sets pertaining to foreign particles and data sets pertaining to recessed defects. In contrast, the data obtained as a result of a laser beam being radiated obliquely onto a wafer contain only data sets pertaining to the distribution of foreign particles.

Figure 9A:
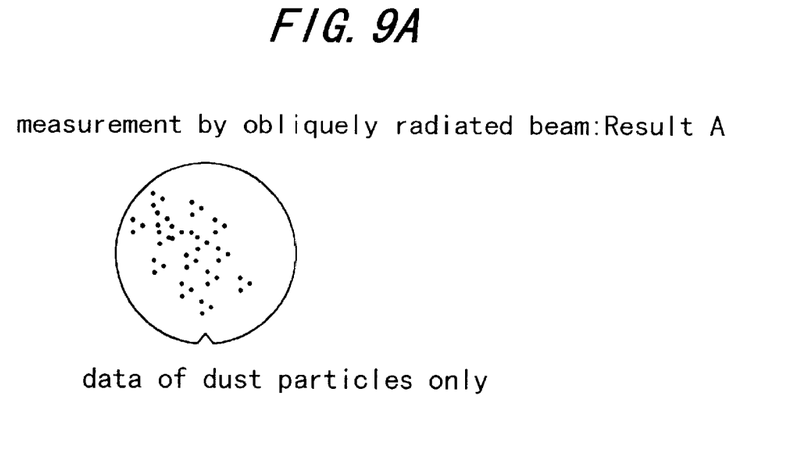
FIG. 9A through FIG. 9C show principle for computing the distribution of recessed defects over a real wafer.
Figure 9B:
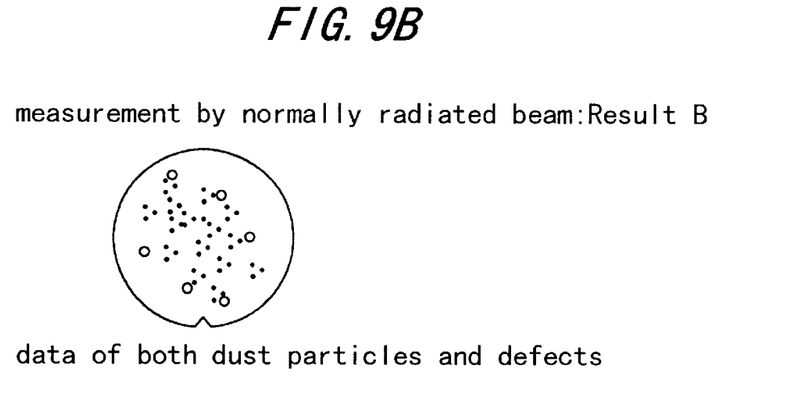
Figure 9C:
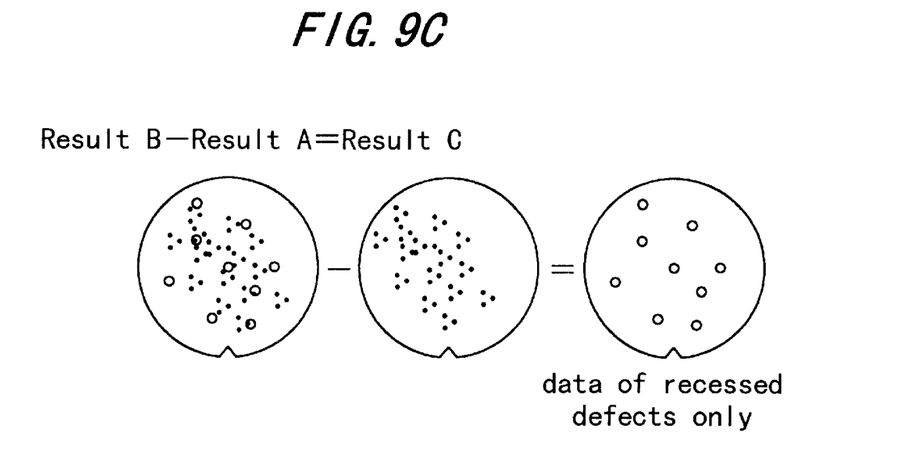

As shown in FIGS. 9A through 9C, the data (Result C) pertaining to only recessed defects in a wafer can be obtained by means of subtracting the data (Result A) that have been obtained as a result of a laser beam being radiated obliquely onto a wafer, from the data (Result B) that have been obtained as a result of a laser beam being radiated onto a wafer from a normal direction. This technique enables sharp distinction of foreign particles from recessed defects and acquisition of the distribution of recessed defects located in a wafer.

Third Embodiment

In a process of manufacturing a semiconductor device, recessed defects formed in a semiconductor wafer are usually inspected, and selected wafers are loaded into processing steps. The step of measuring the distribution of recessed defects formed in a semiconductor wafer, which has been described in connection with the first and second embodiments, is used in an inspection step to be performed before a semiconductor wafer is loaded into processing steps. A predetermined wafer processing step and an assembly step are performed after such an inspection step. According to such a method of manufacturing a semiconductor device, a semiconductor wafer—in which inappropriate recessed defects have arisen during the course of fabrication of a semiconductor device—can be removed before it is loaded into processing steps. Thus, factors which would otherwise induce failures can be removed in advance, thereby improving the manufacturing yield of a semiconductor device. Further, a semiconductor device manufactured through such manufacturing processes is characterized by stable characteristics and high reliability.

The step of measuring recessed defects formed in a semiconductor wafer can be performed not only in the inspection step to be performed before a wafer is loaded into a semiconductor wafer processing step, but also at any position in the course of semiconductor wafer processing step. For example, after deposition of a dielectric film, such as a silicon oxide film, on a semiconductor wafer, the distribution of recessed defects formed in the dielectric film can be examined. Further, the step can be employed in a step of inspecting a resist film which has been applied over a semiconductor wafer, in a photolithography process. As mentioned above, so long as the step of measuring recessed defects is performed in the course of the wafer processing step, the distribution of recessed defects which have arisen in the course of the wafer processing step can be grasped. As a result, semiconductor wafers in which defects have arisen can be removed in advance, thereby improving the manufacturing yield of a semiconductor device. Further, a semiconductor device manufactured through such manufacturing processes is characterized by stable characteristics and high reliability.

The inspection step of inspecting recessed defects according to the present invention can be used not only in a process of manufacturing a semiconductor device, but also in a process of manufacturing another device, such as a liquid-crystal panel.

As has been described, the semiconductor inspection system according to the present invention yields an advantage of ability to sharply distinguish foreign particles located on a substrate to be measured from recessed defects formed in the same, thereby readily providing data pertaining to the distribution of recessed defects located in the substrate.

In the method of manufacturing a semiconductor device according to the present invention, recessed defects formed in a semiconductor wafer are inspected during a process for fabricating a semiconductor device, through use of the semiconductor inspection system, thereby improving the manufacturing yield of a semiconductor device and the reliability of the same.

Obviously many modifications and variations of the present invention are possible in the light of the above teachings. It is therefore to be understood that within the scope of the appended claims the invention may by practiced otherwise than as specifically described.

The entire disclosure of a Japanese Patent Application No. 2000-090920, filed on Mar. 29, 2000 including specification, claims, drawings and summary, on which the Convention priority of the present application is based, are incorporated herein by reference in its entirety.

What is claimed is:

1. A semiconductor device inspection system comprising:
   a laser beam radiation section for radiating a laser beam onto a semiconductor wafer to be measured;
   a detection section which detects light scattered from foreign particles or recessed defects formed in the semiconductor wafer, as a result of a laser beam being radiated onto the semiconductor wafer, and converts the detected scattered light into an electric signal; and
   a control section for processing the electric signal in the form of data, said control section outputting information about the recessed defects formed in the semiconductor wafer, by means of subtracting the data pertaining to only the foreign particles located on the semiconductor wafer from the data pertaining to both the foreign particles and recessed defects formed in the semiconductor wafer.

2. The semiconductor inspection system according to claim 1, wherein the data pertaining to solely the foreign particles located on the semiconductor wafer are prepared by means of referring to a sensitivity calibration curve representing a relationship between sizes of foreign particles and intensity of light scattered from the foreign particles, and
   the data pertaining to both the foreign particles and recessed defects formed in the semiconductor wafer are prepared by means of referring to a sensitivity calibration curve representing a relationship between recessed defects and intensity of light scattered from the recessed defects.

3. The semiconductor inspection system according to claim 2, wherein the sensitivity calibration curve representing a relationship between sizes of foreign particles and intensity of light scattered from the foreign particles is prepared through use of a reference wafer to which foreign particles are artificially caused to adhere, and
   the sensitivity calibration curve representing a relationship between recessed defects and intensity of light scattered from the recessed defects is prepared through use of a reference wafer in which recessed defects are artificially formed.

4. A semiconductor device inspection system comprising:
   a laser beam radiation section for radiating a laser beam onto a semiconductor wafer to be measured;
   a detection section which detects light scattered from foreign particles or recessed defects formed in the semiconductor wafer as a result of a laser beam being radiated onto the semiconductor wafer and converts the detected scattered light into an electric signal; and
   a control section for processing the electric signal in the form of data, wherein
   the laser beam radiation section can radiate a laser beam onto the primary surface of the semiconductor wafer by selection of either a normal direction or an oblique direction, and
   the control section can output information about the recessed defects formed in the semiconductor wafer, by means of subtracting the data pertaining to only the foreign particles located on the semiconductor wafer from the data pertaining to both the foreign particles and recessed defects formed in the semiconductor wafer.

5. The semiconductor device inspection system according to claim 4, wherein the data pertaining to only foreign particles located on the semiconductor wafer are prepared by means of a laser beam being radiated onto the primary surface of the semiconductor wafer in an oblique direction relative to the primary surface, and
   the data pertaining to both foreign particles and recessed defects formed in the semiconductor wafer are prepared by means of a laser beam being radiated onto the primary surface of the semiconductor wafer in a normal direction relative to the primary surface.

6. A method of manufacturing a semiconductor device comprising the steps of:
   radiating a laser beam onto a semiconductor wafer to be measured;
   detecting light scattered from foreign particles or recessed defects formed in the semiconductor wafer, as a result of a laser beam being radiated onto the semiconductor wafer and converting the detected scattered light into an electric signal;
   processing the electric signal in the form of data; and
   outputting information about the recessed defects formed in the semiconductor wafer by means of subtracting the data pertaining to only the foreign particles located on the semiconductor wafer from the data pertaining to both the foreign particles and recessed defects formed in the semiconductor wafer.

7. The method of manufacturing a semiconductor device according to claim 6, wherein the data pertaining to solely the foreign particles located on the semiconductor wafer are prepared by means of referring to a sensitivity calibration curve representing a relationship between sizes of foreign particles and intensity of light scattered from the foreign particles, and
   the data pertaining to both the foreign particles and recessed defects formed in the semiconductor wafer are prepared by means of referring to a sensitivity calibration curve representing a relationship between recessed defects and the intensity of light scattered from the recessed defects.

8. The method of manufacturing a semiconductor device according to claim 7, wherein the sensitivity calibration curve representing a relationship between sizes of foreign particles and intensity of light scattered from the foreign particles is prepared through use of a reference wafer to which foreign particles are artificially caused to adhere, and the sensitivity calibration curve representing a relationship between recessed defects and intensity of light scattered from the recessed defects is prepared through use of a reference wafer in which recessed defects are artificially formed.

9. A method of manufacturing a semiconductor device comprising the steps of:

radiating a laser beam onto a semiconductor wafer to be measured in a normal direction, detecting light scattered from foreign particles or recessed defects formed in the semiconductor wafer, as a result of a laser beam being radiated onto the semiconductor wafer, and converting the detected scattered light into an electric signal, to thereby prepare data pertaining to both foreign particles and recessed defects formed in the semiconductor wafer;

radiating a laser beam onto the primary surface of the semiconductor wafer in an oblique direction, detecting the light scattered from foreign particles located on the semiconductor wafer when the laser beam is radiated onto the foreign particles, and converting the detected scattered light into an electric signal, to thereby prepare data pertaining to solely foreign particles located on the semiconductor wafer; and outputting information about the recessed defects formed in the semiconductor wafer by means of subtracting the data pertaining to only the foreign particles located on the semiconductor wafer from the data pertaining to both the foreign particles and recessed defects formed in the semiconductor wafer.

* * * * *